United States Patent [19]

Li

[11] Patent Number: 5,075,511

[45] Date of Patent: Dec. 24, 1991

[54] PROCESS AND ALKYLMERCAPTOAMINE CATALYST FOR PRODUCTION OF BISPHENOL-A

[75] Inventor: Simon M. Li, Houston, Tex.

[73] Assignee: Shell Oil Company, Houston, Tex.

[21] Appl. No.: 540,396

[22] Filed: Jun. 19, 1990

Related U.S. Application Data

[60] Continuation of Ser. No. 309,503, Feb. 13, 1989, abandoned, which is a division of Ser. No. 925,779, Oct. 30, 1986, Pat. No. 4,820,740.

[51] Int. Cl.$^5$ .................. C07C 39/12; C07C 39/16
[52] U.S. Cl. ......................... 568/727; 568/728
[58] Field of Search .................. 564/500; 568/727, 728

[56] References Cited

U.S. PATENT DOCUMENTS

| | | |
|---|---|---|
| 2,807,653 | 9/1957 | Filbey et al. .......................... 260/619 |
| 3,394,089 | 7/1968 | McNutt et al. ....................... 260/2.2 |
| 3,642,900 | 2/1972 | Sakai et al. ........................... 260/583 |
| 3,760,006 | 9/1973 | Gammill et al. .................. 260/619 A |
| 4,053,522 | 11/1977 | McClure .......................... 260/619 A |
| 4,294,995 | 10/1981 | Faler et al. ........................... 568/728 |
| 4,346,247 | 8/1982 | Faler .................................... 568/728 |
| 4,369,293 | 1/1983 | Heydenreich et al. ........... 525/333.5 |
| 4,423,252 | 12/1983 | Maki et al. ........................... 568/728 |
| 4,424,285 | 1/1984 | DiGiulio .............................. 521/56 |
| 4,455,409 | 6/1984 | Faler et al. .......................... 525/351 |
| 4,478,956 | 10/1984 | Maki et al. ............................ 521/32 |
| 4,584,416 | 4/1986 | Pressman et al. .................... 568/727 |

FOREIGN PATENT DOCUMENTS

| | | | |
|---|---|---|---|
| 1863 | 5/1979 | European Pat. Off. | ............ 568/728 |
| 7420565 | 3/1969 | Japan . | |
| 81142227 | 7/1980 | Japan . | |
| 57-144252 | 3/1981 | Japan . | |
| 56-131534 | 12/1981 | Japan . | |
| 1539186 | 1/1979 | United Kingdom . | |
| 1539463 | 1/1979 | United Kingdom . | |

OTHER PUBLICATIONS

Chem. Abstracts vol. 96, entry 86122h.

*Primary Examiner*—Thurman K. Page
*Assistant Examiner*—Peter F. Kulkosky

[57] ABSTRACT

Bisphenol-A is prepared by reacting an excess of phenol with acetone in the presence of a modified sulfonic acid cationic exchange resin catalyst having a plurality of sulfonic acid sites of the general formula

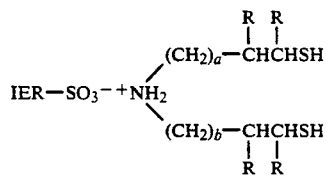

in which IER represents the ionic exchange resin backbone, each a and b is an integer from 0 to about 5, and each R is selected independently from H, OH, SH and alkyl groups. The catalyst exhibits high activity and selectivity at moderate reaction temperatures, low production of colored impurities, and high stability.

10 Claims, 1 Drawing Sheet

FIG.1 (1-CONV.) vs. 1/WHSV AT 75°C

FIG.2 (1-CONV) vs. p,p'/o,p' SELECTIVITY AT 75°C

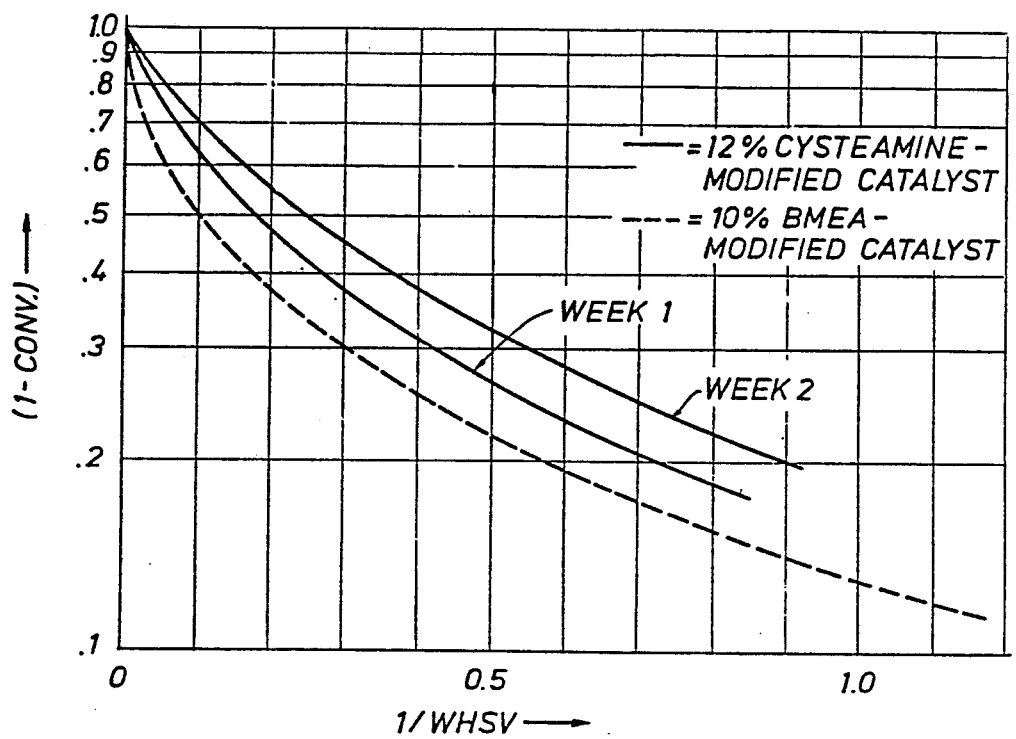
FIG.1 (1-CONV.) vs. 1/WHSV AT 75°C
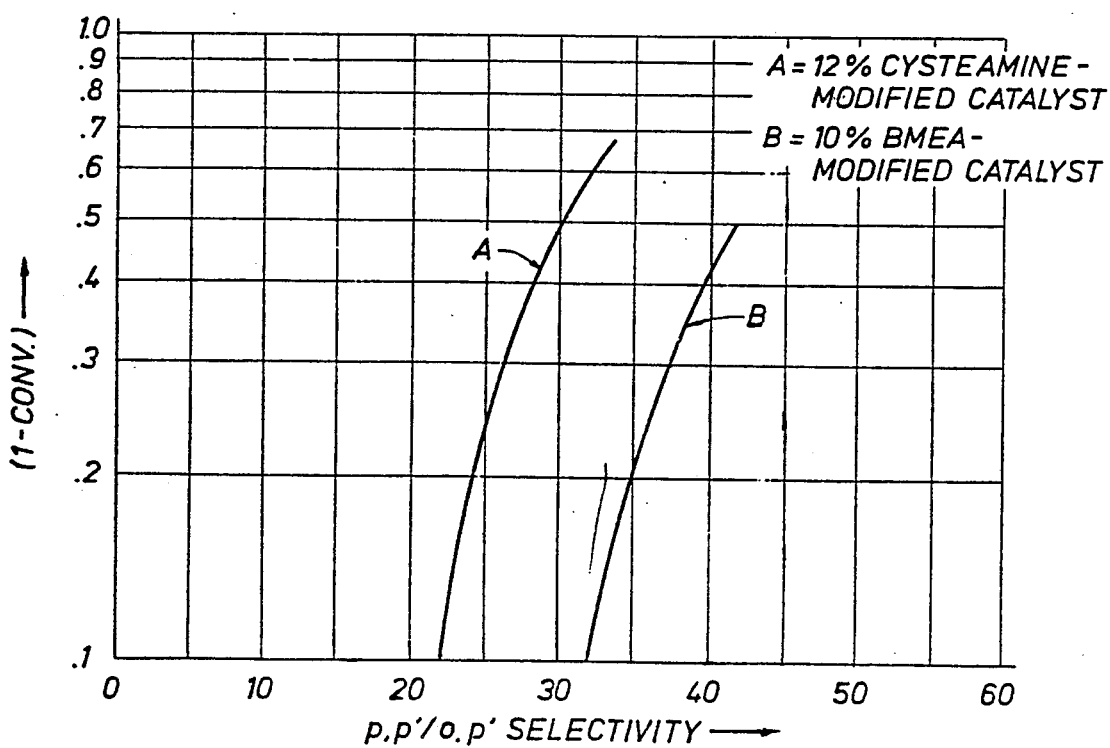
FIG.2 (1-CONV.) vs. p,p'/o,p' SELECTIVITY AT 75°C

PROCESS AND ALKYLMERCAPTOAMINE CATALYST FOR PRODUCTION OF BISPHENOL-A

This is a continuation of application Ser. No. 309,503, filed Feb. 13, 1989, now abandoned was a divisional of application Ser. No. 925,779, filed Oct. 30, 1986, now U.S. Pat. No. 4,820,740.

BACKGROUND OF THE INVENTION

This invention relates to the production of bisphenol-A. In one aspect, the invention relates to cationic exchange resins useful as catalysts for the reaction of phenol and acetone to produce bisphenol-A.

Bisphenol-A (BPA), an important base chemical used as a starting material for polyepoxide and polycarbonate resins, is commercially prepared by reacting phenol and acetone in the presence of an acidic catalyst such as sulfuric acid, hydrochloric acid or a sulfonic acid cationic exchange resin. Cationic exchange resins offer the advantage, over free acid catalysts, of safer and more convenient handling. For certain applications such as polycarbonate production, it is particularly important to produce BPA which has extremely high purity, particularly with respect to impurities which add color to the BPA. Efforts have been made to improve the quality of the BPA product and the efficiency of the BPA process by modifying the catalyst.

It is known that mercaptan compounds, used with either cationic exchange resins or free acid, are effective promoters of the phenol-acetone condensation reaction which produces BPA. When soluble mercaptans such as ethyl mercaptan are used as promoters, contamination of the product BPA with sulfur is often an undesirable side effect, necessitating additional process steps for removal and recovery of the mercaptans. The contamination problem can be alleviated by chemically bonding an amino mercaptan promoter to the exchange resin catalyst by partial neutralization or reaction of the sulfonic acid groups of the resin by the reactive group of the mercaptan containing compound.

Various mercaptan group-containing materials have been used as such chemically-bonded promoters for cationic exchange resin catalysts, including alkyl mercaptoalcohols (U.S. Pat. No. 3,049,568), $C_1$-$C_4$ alkyl mercaptoamines (U.S. Pat. No. 3,394,089) and N-aminoorganomercaptan groups (U.S. 4,584,416). Since both the catalyst acidity and the presence of mercaptan groups are factors in the effectiveness of the catalyst, the one-for-one exchange of sulfonic acid sites on the ionic exchange resin for mercaptan groups represents a compromise of catalyst efficiency. It would be desirable to have ionic exchange resin catalysts for BPA production which are highly active at moderate reaction temperatures, highly selective, not subject to degradation under typical reaction conditions, and capable of producing BPA low in colored impurities.

It is therefore one object of the invention to prepare a cationic exchange resin catalyst which exhibits high activity and selectivity. It is a further object to provide a chemically-modified cationic exchange resin catalyst with enhanced stability. It is a further object to produce high quality BPA using a novel modified sulfonic acid ionic exchange resin catalyst.

BRIEF DESCRIPTION OF THE DRAWING

FIG. 1 compares acetone conversion for a bis-3-(mercaptoethyl)-amine-modified catalyst over a two week period.

FIG. 2 shows the presence of by-products in the reaction product mixtures for the invention catalyst compared with that of the cysteamine-modified catalyst.

BRIEF DESCRIPTION OF THE INVENTION

According to the invention, BPA is prepared by the reaction of acetone and phenol in the presence of a polyfunctional mercaptoamine-modified cationic exchange resin catalyst. The catalyst is characterized by at least partial substitution of the ionic exchange resin with an alkylmercaptoamine group having at least two alkylmercaptan branches. The catalyst is preferably prepared by mercaptoamine addition to the sulfonyl groups of a cationic ion exchange resin and can be described by the following formula:

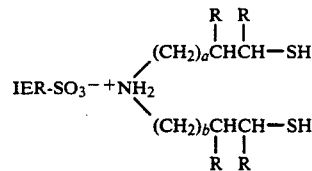

in which IER represents the ionic exchange resin backbone, each of a and b is an integer from 0 to about 5 and each R is selected independently from H, OH, SH, and alkyl groups. As can be seen from the formula, the invention catalyst contains a higher acidity density per given mercaptan concentration, or a higher mercaptan concentration per given residual acidity density, as compared to cationic exchange resin catalysts modified with monofunctional mercaptan promoters. The catalyst exhibits high activity and selectivity at moderate reaction temperatures, low production of colored impurities and good stability.

DETAILED DESCRIPTION OF THE INVENTION

The invention catalyst can be described by the formula

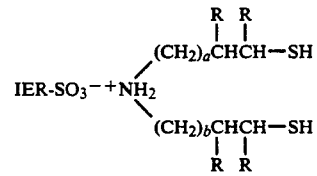

in which IER represents the backbone of an ionic exchange resin, each of a and b is an integer from 0 to about 5 and each R is selected independently from H, OH, SH and alkyl groups. The ionic exchange resin can be any insoluble strong-acid cationic exchange resin, preferably an aromatic sulfonic acid resin having a cation-exchange capacity of at least about 0.5 and preferably at least 2.0 meq/g dry weight. Particularly suitable are strong acid sulfonated styrene-divinylbenzene copolymer resins. Such ionic exchange resins are commercially available in gel and macroreticular form as, for example, Dowex 50 resins, Amberlite IR resins, Dowex MSC-1 resins, Amberlyst 15 resins and Duolite C-20 resins. The catalyst is suitably employed as 15-100 mesh resin beads in a fixed bed.

The commercially-available aromatic sulfonic acid resins are generally handled as sodium salts. These acid salts are preferably converted to acid form by conventional means prior to treatment with the chosen aminomercaptan modifying agent.

The preparation of the aminomercaptan modifier can be carried out by halogenating a diolefinic amino compound of the general formula

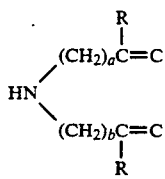

in which a, b and R are as described above.

Such compounds include, for example, the diallylamine in which a and b are 1. Alternately, the modifier can be prepared by starting with a secondary amine containing multiple alkyl halides of the general formula

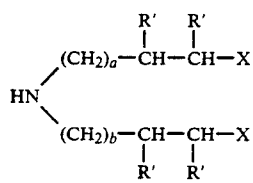

in which R' is selected independently from H, Cl, Br, I and alkyl groups, and each X is independently chosen from Cl, Br and I. Such compounds include, for example, the bis-2-haloethylamine. The above halogen-containing amine salt, for example the bis-2-halogenethyl amine hydrochloride salt, is reacted with sodium thioacetate in an alcoholic medium such as ethanol. The resulting bis-(2-thioacetylethyl)acetamide can be acid neutralized by hydroalysis since Oct. 30, 1986 and reacted with sulfonyl groups of the cationic exchange resin by reflux together in aqueous alcoholic solution with an optional reducing agent such as triphenyl phosphine. The modified resin is then washed with an aqueous alcohol in solution and dried in a vacuum at about 50-100° C.

The currently preferred modified cationic exchange resin catalysts of the invention can be described by the formulas

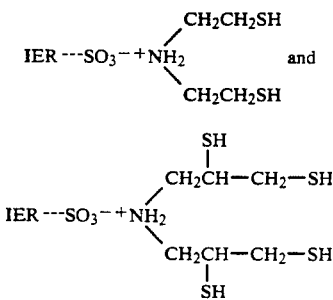

The modified IER catalyst will generally have from about 2 mole percent to about 50 mole percent of chemically-modified sulfonic acid units, preferably about 3 to about 25 mole percent.

The invention catalyst is useful in the preparation of a bisphenol by the reaction of a ketone, such as acetone, ethyl methyl ketone, isobutyl methyl ketone, acetophenone, cyclohexanone, 1,3-dichloroacetone and the like, with a phenol such as phenol, o-cresol, m-cresol, o-chlorophenol, m-chlorophenol, o-t-butylphenol, 2,5-xylenol, 2,-5-di-t-butylphenol, o-phenylphenol and the like. The commercially-significant utility of the catalyst is in the reaction of acetone with phenol to prepare bisphenol-A. In the cationic exchange resin-catalyzed preparation of BPA, an excess of phenol, generally about 5 to about 20 moles per mole of acetone, is desirable for high acetone conversion. The condensation reaction is carried out at temperatures in the range of about 30 to about 120° C., preferably about 45 to 100° C. The reaction is generally carried out under atmospheric pressure. Solvents or diluents are not necessary except at low reaction temperatures. The reaction can be carried out in batch or continuous form. The modified cationic exchange resin catalyst can be used as a slurry with the reactants in batch reactions or in a fixed bed in a continuous process.

The reaction time depends upon the reaction temperature and other reaction conditions. In a batch process, a reaction time within the range of about 0.5 to 20 hours will generally achieve desired conversion. In a continuous operation using a fixed catalyst bed, a flow rate with the range of 0.1 to 12.0, preferably 0.5 to 6, weight per hour per bed weight will generally be suitable. The product mixture is then separated from the catalyst, and the BPA can be recovered by means such as flash distillation to remove water, phenol and other volatile impurities. Purification of the BPA can be effected by distillation, recrystallization, solvent washing, and the like.

Carrying out the production of BPA in the presence of the modified sulfonic acid exchange resin described herein results in a BPA product having a low level of colored impurities. The catalyst is highly active and stable at reaction temperatures of below about 100° C. and has been found to exhibit high activity at reaction temperatures as low as 65° C.

The following examples illustrate preparation of exemplary modified catalysts and use of the invention modified catalysts in the preparation of BPA.

EXAMPLE 1

This example illustrates preparation of bis-2-(thioacetylethyl)-acetamide and subsequent in-situ modification of a cationic exchange resin with the bis-2-(mercaptoethyl)amine.

Sodium thioacetate was prepared by adding slowly 349.21 g of sodium ethoxide-ethanol solution (at 14.88% w solution) into 58.05 g of distilled thioacetic acid in an ice bath under nitrogen atmosphere. 367.94 g of the above solution was then added to 320.16 g of a bis-2-[chloroethyl]-amine hydrochloride/ethanol solution (12.5% w solution) under nitrogen atmosphere. The well-mixed reaction mixture was heated and refluxed for about 45 minutes. The resulting slurry was filtered, and the filtrate was subjected to vacuum distillation at temperatures below 80° C. to remove most of the solvent.

164.77 g of reagent grade acetone was added to the cooled residue to dissolve the product and precipitate additional salt. After a second filtration, the filtrate was vacuum distilled at below 60° C. to remove volatiles. 56.71 g of final product residue having 5.17% w nitrogen content based on Kjeldahl analysis was recovered.

10.16 g of the reaction product from step 1, 146.20 g of wet DOWEX® MSC-1, 74.64 g reagent methanol and 895.36 g of deionized water were charged into a 2L flask equipped with stirrer, condenser and thermometer. The mixture was heated to reflux for 7 hours. After standing overnight, the slurry was washed/filtered with deionized water, methanol and deionized water several times. 157.33 g of wet product resin catalyst was recovered. Analysis showed 13.5% w and 15.7% w sulfur on the starting and product resin catalyst, respectively.

The wet resin catalyst was dried in a vacuum oven (at about 70° C. for 24 hours) when used for batch reactions, or used as wet resin in continuous reactions. In the latter case, the dry feed serves to remove moisture as well from the invention resin catalyst during the initial purge period.

EXAMPLE 2

This example illustrates the preparation of bis-2,3-(dihalidepropyl) amine hydrochloride salt. 128.6g bromine was slowly added to a mixture of 53.7 g of diallylamine hydrochloride and 402.6 g of methylene chloride in a 1L flask with nitrogen blanketing. The system temperature was controlled to 10–20° C. in an ice water bath. Upon completion of bromine addition, the slurry mixture was further allowed to mix at room temperature overnight, and product was separated from the mother liquor, washed with additional methylene chloride and dried. The product was titrated with silver nitrate at room temperature. Total free halide found was 2.087 meq/g (theny: 2.206 meq/g).

EXAMPLE 3

This example shows the results in terms of product properties in a batch reaction using the invention modified ionic exchange resin catalyst and compares the product with those from processes in which other catalysts are used. The invention processes (G-1, G-2, MR-1) were carried out with catalysts made according to Example 1. The reaction conditions included a phenol to acetone ratio of 12:1 molar, a 2:1 weight ratio of catalyst to acetone, and a reaction temperature of 70° C. Results are tabulated in Table 1. Although generalizations are difficult from batch data, the invention BMEA-modified catalyst generally exhibits superior selectivity for the p,p' isomer, compared with the cysteamine-modified catalyst, and essentially equivalent reactivity under batch conditions.

EXAMPLE 4

This example compares the activity and performance of the invention modified cationic exchange resin catalyst and a cysteamine-modified catalyst. The invention catalyst was a Dowex® MSC-1 cationic exchange resin modified by 10% substitution with bis-2-(mercaptoethyl)amine (BMEA) and the comparison catalyst was a Dowex®MSC-1 cationic exchange resin modified by 12% substitution with cysteamine groups ($NH_2CH_2CH_2SH$). Continuous runs were performed at 70° C. using a phenol to acetone ratio of 12:1. FIG. 1 compares acetone conversion, a measure of catalyst activity, for the two catalysts in a continuous BPA preparation process. FIG. 1 illustrates the activity of t BMEA-modified catalyst over a two-week period, versus the activity of the cysteamine-modified catalyst over a two-week period, with declining with time. The results show the superior activity and stability of the invention catalyst. FIG. 2 shows the presence of by-products in the reaction product mixture for the invention catalyst compared with the cysteamine-modified -.catalyst. Use of the BMDA-modified catalyst resulted in higher p,p'/o,p' selectivity (FIG. 2). In general, the BMEA-modified catalyst under continuous reaction conditions exhibits superior performance in terms of selectivity, stability and BPA color, while the cysteamine catalyst appeared to yield marginally lower levels of two common BPA by-products of uncertain identity.

TABLE 1

| Catalyst | Modifier | % Modifier | % p,p' BPA | % o,p' BPA | % BPX | % Codimer (Impurity) | % Conv Basis DMK | % Conv Basis BPA | % Conv by Recovery |
| --- | --- | --- | --- | --- | --- | --- | --- | --- | --- |
| G-1[2] | $NH(CH_2CH_2SH)_2$ (ionic) | 10.8 | 18.0 | 0.50 | 0.09 | 0.01 | 83.7 | 95.5 | 96 |
| MR-1 | $NH(CCSHCSH)_2$ (ionic) | 10.0 | 12.7 | 0.35 | 0.05 | 0.02 | 65.3 | 68.3 | 56 |
| G-2[1] | $NH(CH_2CH_2SH)_2$ (ionic) | 13.6 | 14.1 | 0.40 | 0.09 | — | 84.6 | 77.5 | — |
| MR-2 | Non-modified | 0 | 4.3 | 0.65 | 0.03 | 0.25 | 19.3 | 27.6 | 17 |
| MR-3 | Free $CO_2HCH_2CH_2SH$ | 14.0 | 16.0 | 0.36 | 0.09 | 0.02 | 92.2 | 98.9 | 20[3] |
| G-3[2] | Non-modified | 0 | 9.8 | 1.43 | 0.14 | 0.43 | 81.0 | 63.5 | — |
| MR-4 | Cysteamine (ionic) | 21.0 | 11.2 | 0.24 | 0.08 | 0.01 | 62.7 | 61.0 | 58 |
| G-4[1] | Non-modified | 0 | 10.3 | 1.20 | 0.08 | 0.50 | 64.8 | 63.8 | 38 |
| G-5[2] | Free $CO_2HCH_2CH_2SH$ | 14.0 | 24.6 | 0.72 | 0.13 | 0.04 | 97.9 | >100 | 114[3] |
| G-6[1] | Free $CO_2HCH_2CH_2SH$ | 14.0 | 18.1 | 0.58 | 0.13 | 0.05 | >98.0 | 98.8 | 76[3] |
| G-7[2] | Cysteamine (ionic) | 10.0 | 15.2 | 0.53 | 0.08 | 0.03 | 89.7 | 82.9 | — |
| G-8[1] | Cysteamine (ionic) | 30.6 | 14.2 | 0.34 | 0.08 | 0.01 | 71.2 | 76.6 | 81 |

[1]4% crosslinked DVB.
[2]2% crosslinked DVB.
[3]Stripping free acidic mercaptan results in product degradation and inconsistent results.

I claim:

1. A process for preparing a bisphenol comprising contacting at least two moles per mole of a phenol of a ketone in the presence of a sulfonated cationic exchange resin of general formula

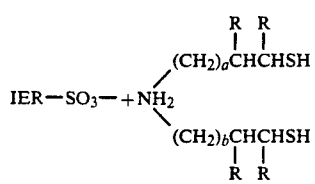

in which IER is the backbone of a sulfonated cationic exchange resin having sulfonic acid sites, each of a and b is an integer from 0 to about 5 and each R is selected independently from H, OH, SH and alkyl, said sulfonated cationic exchange resin having at least about 2% of sulfonic acid sites ionically bound to an aminomercaptan group of the formula

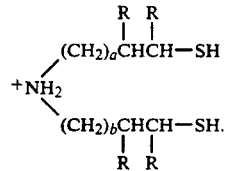

2. The process of claim 1 in which the bisphenol is bisphenol-A, the phenol is phenol, and the ketone is acetone.

3. The process of claim 2 in which the cationic exchange resin is a gel-type resin.

4. The process of claim 2 in which the cationic exchange resin is a macroreticular-type resin.

5. The process of claim 2 in which the ionically-bound group can be described by the formula

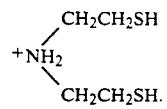

6. The process of claim 2 in which the ionically-bound group can be described by the formula

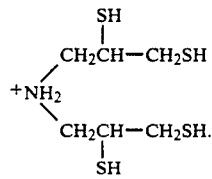

7. The process of claim 2 in which about 3 to about 25 mole percent of the sulfonic acid sites of the cationic exchange resin are substituted with the ionically-bound group.

8. The process of claim 2 in which the ionic exchange resin IER is a styrene-divinylbenzene copolymer resin.

9. The process of claim 8 in which about 2 to about 50 mole percent of the sulfonic acid sites of the cationic exchange resin are substituted with the ionically-bound group.

10. The process of claim 2 in which said contacting is carried out at a temperature within the range of about 45 to about 100° C.

* * * * *